United States Patent [19]

Sweeney, III

[11] 4,398,532

[45] Aug. 16, 1983

[54] INSERTION DEVICE FOR A DIAPHRAGM

[76] Inventor: William J. Sweeney, III, 912 Fifth Ave., New York, N.Y. 10021

[21] Appl. No.: 215,626

[22] Filed: Dec. 12, 1980

[51] Int. Cl.³ .............................................. A61F 5/46
[52] U.S. Cl. ...................................... 128/127; 604/16
[58] Field of Search ................................. 128/127–129, 128/263, 270, 285; 604/11–12, 14–18, 285

[56] References Cited

U.S. PATENT DOCUMENTS

| | | | |
|---|---|---|---|
| 2,141,040 | 12/1938 | Holt | 128/127 |
| 2,376,193 | 5/1945 | Salvin | 128/127 |
| 2,832,342 | 4/1958 | Wingenroth | 128/263 |
| 3,068,867 | 12/1962 | Bletzinger et al. | 128/263 |
| 3,139,886 | 7/1964 | Tallman et al. | 128/263 |
| 4,271,835 | 6/1981 | Conn et al. | 128/270 |

*Primary Examiner*—C. Fred Rosenbaum

*Attorney, Agent, or Firm*—Weingram & Klauber

[57] ABSTRACT

An insertion device for a diaphragm is provided. The device comprises an elongated hollow member which has a chamber for longitudinally holding a diaphragm. An opening is provided in one end of the member through which the diaphragm is dispensed. A plunger means slidable within the hollow member is at the other end of the member and used for dispensing the diaphragm through the opening. An indicia means is provided on the plunger for indicating the proper orientation of the diaphragm for insertion. The chamber preferably contains a disposable diaphragm and a spermacidal agent. An indicia means may also be provided for indicating the complete release of the diaphragm from the opening. A removable closure means, e.g. self-sticking tape, may be provided for sealing the opening.

27 Claims, 9 Drawing Figures

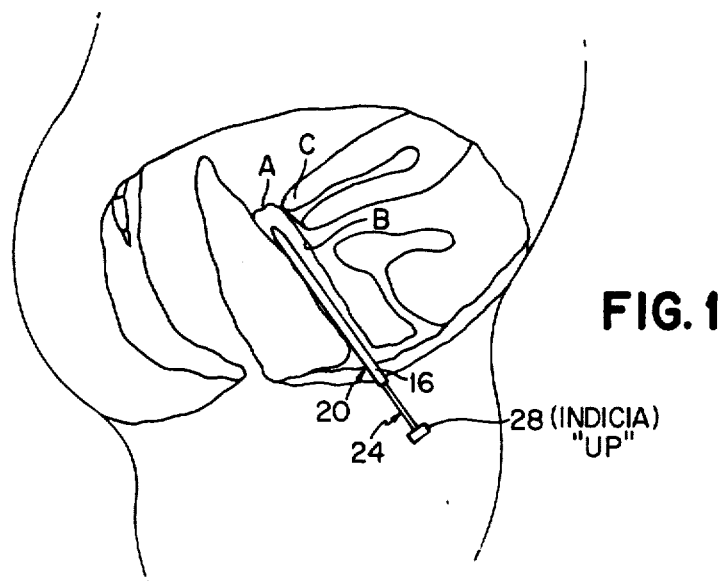
FIG. 1
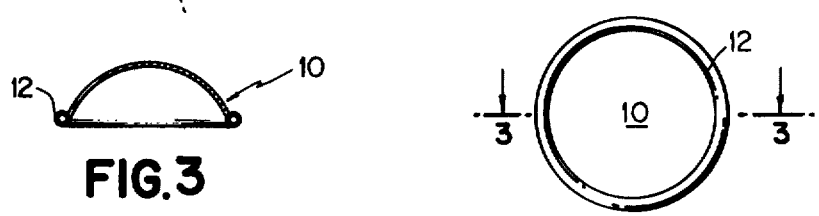
FIG. 3  FIG. 2
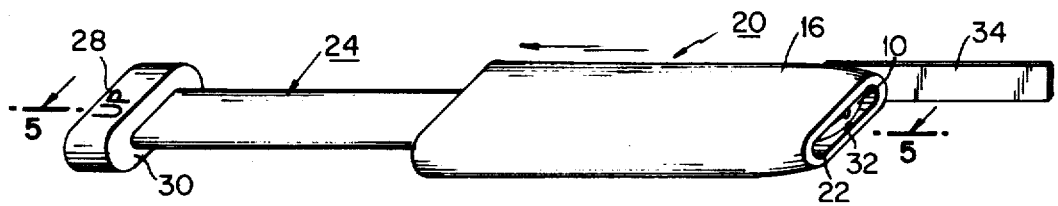
FIG. 4
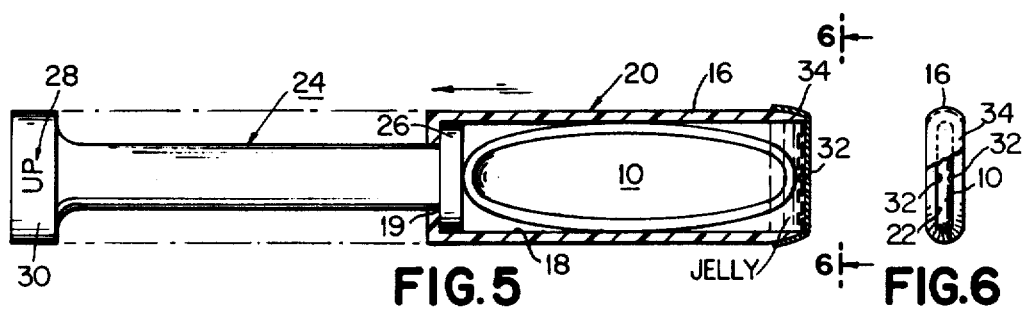 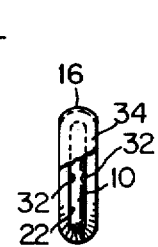
FIG. 5  FIG. 6

INSERTION DEVICE FOR A DIAPHRAGM

BACKGROUND OF INVENTION

1. Field of the Invention

The present invention relates to a device for inserting a diaphragm into the vaginal canal and into position covering the cervix. In particular, this invention relates to a device for inserting a disposable diaphragm, which has been treated with spermacidal agent, in the proper orientation and position, utilizing means to insure that sterility is preserved.

2. Description of the Prior Art

Various birth control methods have been proposed in recent years. One widely known method of birth control is the oral administration of birth control pills. This systematic suppression of conception through the use of hormones, while being effective, often has undesirable side effects on the user, particularly older women. An additional problem which has limited the complete acceptance of such contraceptive pills is the unknown long range effects of the use of such hormones on the human body.

Of more recent date, the introduction of intra-uterine devices (IUD), has provided an alternative to birth control pills. Such devices afford effective contraception without causing the undesirable side effects produced by birth control pills. However, since the IUD is permanently placed in the uterus to provide a mechanical obstacle to insemination, it may not be tolerated by the tissue and mucous membrane which surround it. Such a condition often results in the dislodgement of the IUD and/or irritation and insult to the tissue of the uterus posing a hazard to the health of the user.

It is also known to use a flexible non-permeable diaphragm usually in conjunction with a spermacidal agent as a method of contraception. The diaphragm is lodged in the vaginal canal at the base of the cervix and is retained in this position by virtue of the surrounding contractual wall tissue and the resilience of the diaphragm.

Diaphragms have met with less acceptance by potential users than would be indicated by their contraceptive effectiveness because of three problems:

1. Inconvenience of use. Diaphragms are normally used in conjunction with a spermacidal agent, either a jelly or foam. The spermacidal agent must be applied within 20 minutes of intercourse in order to have maximum effectiveness. This poses a problem for the user in that the spermacidal agent normally comes in contact with the hands and fingers leaving them greasy and requiring the users to wash their hands and/or other parts of their anatomy to remove excess quantities of this spermacidal agent after insertion of the diaphragm.

2. Sanitary problems relating to frequent insertion and removable of the diaphragm provides a source of contamination of the vaginal canal and the uterus.

3. Esthetic problems relating to storage. Diaphragms normally have useful lives of six months or longer and are used frequently during that time. After repeated use, the diaphragms tend to take on an unpleasant odor. This odor makes it inconvenient to carry the diaphragm in the users purse or handbag where it would be most readily available.

Additionally, insertion of the diaphragm is often difficult, especially if it has been coated with the spermacidal agent. It requires the user to assume awkward body positions and engage in awkward manipulation in order to properly position the diaphragm. With respect to insertion of the diaphragm, one of the problems involves the proper orientation and positioning. Such orientation and positioning of the diaphragm is necessary since insemination cannot be prevented unless the diaphragm covers the end of the cervix.

Many insertion devices or applicator instruments are known which assist in placing the diaphragm into the vaginal canal in the proper orientation and position near the cervix.

One type of device for inserting a diaphragm is described in U.S. Pat. No. 3,786,807 to Dubin. Dubin describes a disposable diaphragm and reuseable insertion-removal unit which enables the user to easily insert, position and remove the diaphragm. The diaphragm includes a magnetically attractable object embedded in absorbent material. The magnetically attractable object is attracted to or released from the tip of the insertion-removal unit. The insertion-removal unit has a magnet at the end of a plunger-rod. When the plunger-rod is advanced forward, it attracts and hold the diaphragm and when it is retracted, it releases the diaphragm.

Another known device is U.S. Pat. No. 2,141,040 to Holt which describes an applicator device which is tubular. The pessary, which is described as useful in the treatment of infections and disorders of the cervix, uterus and vagina, is placed within an open ended tube. The tube is slightly flattened in section and provided with a piston and a handle on the end thereof. The piston forces the pessary out of the tube into an appropriate position. To insure that the pessary is properly placed it is given a distinctive color on the concave side, so that the tube, which is transparent, can be inserted with the concave side uppermost.

Both of these devices are unsatisfactory in many respects. Dubin requires a specially formed and expensive diaphragm. Additionally, it requires the use of a magnetic element in the diaphragm which may be injurious or cause an infection. Additionally, sterility of the diaphragm is not insured because it is not enclosed in a chamber and must be manually positioned on the end of the applicator. Further, there is no provision for applying, in a sterile manner, a spermacidal agent nor is there provision for indicating the proper orientation of the diaphragm for insertion.

Holt suffers from many of the same deficiencies as Dubin. Holt does provide a means for indicating the proper orientation of the diaphragm, but the means is provided on the tube itself; thus, once the tube is inserted it cannot be determined whether the tube was inserted in the proper orientation or is still in the proper orientation, for the tube is within the vagina. Holt, additionally, requires a specially marked or colored diaphragm.

Both Dubin and Holt do not provide any means for determining whether the diaphragm has been completely released from the insertion device.

Of additional interest are the following U.S. Pat. Nos.:

2,008,380 to Bachmann;
2,101,875 to Schleicher;
2,104,275 to Schleicher;
2,218,009 to Schmitz, Jr.; and
2,444,672 to Prather.

All of these references describe fairly complicated gynecological instruments for insertion of a pessary, generally by someone other than the user. None of these devices provide for enclosing the pessary in a sterile manner and are generally unsuitable for use by the user of the pessary.

None of these prior art references provide an insertion device which can, in a sterile manner, insert a disposable diaphragm treated with a spermacidal agent and provide a device which indicates the proper orientation of the diaphragm and has the capability of indicating the complete release of the diaphragm from the device.

SUMMARY OF THE INVENTION

To overcome some of the aforementioned problems, the present invention provides a unique device for the insertion of a diaphragm into the vaginal canal at the base of the cervix. The device comprises an elongated hollow member having a chamber for longitudinally holding a diaphragm which may be immersed in a spermacidal agent. An opening is provided on one end of the member through which the diaphragm is dispensed. The plunger means is slidable within the hollow member at the other end of the member. The plunger means dispenses the diaphragm through the opening. An indicia means is provided on the plunger for indicating the proper orientation of the diaphragm for insertion.

It is therefore an object of the present invention to provide a device for easily inserting and positioning a contraceptive diaphragm in the vaginal canal.

Yet another object of the present invention is to provide an insertion device which enables one to insert a contraceptive diaphragm in a completely sterile manner.

A further object of the present invention is to provide an insertion device for a contraceptive diaphragm which simultaneously inserts the diaphragm and a spermacidal agent into the vaginal canal.

Another object of the present invention is to provide an insertion device having an indicia means which indicates the proper orientation of the diaphragm for insertion.

Yet another object of the present invention is to provide an insertion device having an indicia means for indicating the complete release of the diaphragm from the insertion device.

Still another object of the present invention is to provide a means for insertion of a contraceptive diaphragm in the proper position without touching the diaphragm, thus providing a substantially sterile environment.

A further object of the present invention is to provide a means for conveniently storing a diaphragm and a spermacidal agent in a sterile portable manner with an extended shelf life.

Another object of the present invention is to provide a means for providing a disposable diaphragm which is relatively economical to manufacture.

Yet another object of the present invention is to provide a means for providing a disposable diaphragm which is relatively easy to use.

Still another object of the present invention is to provide a means for providing a disposable diaphragm which does not require a separate container for a spermacidal agent.

A further object of the present invention is to provide a means for providing a disposable diaphragm which does not require separate application of a spermacidal agent to a diaphragm prior to use.

Yet another object of the present invention is to provide a means for providing a disposable diaphragm which can be conveniently used with a minimum of preparation.

Another object of the present invention is to provide a means for providing a disposable diaphragm which can be conveniently used without having to be viewed by the user during insertion.

Still another object of the present invention is to provide a means for providing a disposable diaphragm which is easily portable.

Yet another object of the present invention is to provide a means for providing a disposable diaphragm which can be hermetically sealed.

Another object of the present invention is to provide a means for providing a disposable diaphragm which is not bulky or inconvenient to carry.

Other objects and advantages will become apparent from the following description taken in conjunction with the accompanying drawings.

BRIEF DESCRIPTION OF DRAWINGS

FIG. 1 is a schematic view of a portion of the female anatomy showing an embodiment of the insertion device of this invention inserted into the vaginal canal preparatory to releasing the diaphragm over the cervix;

FIG. 2 is a plan view of a disposable diaphragm used in the insertion device of this invention;

FIG. 3 is a sectional view of the disposable diaphragm taken along the line 3—3 of FIG. 2;

FIG. 4 is a perspective view of an embodiment of the insertion device of this invention;

FIG. 5 is a longitudinal cross sectional view of the insertion device depicted in FIG. 4 taken along line 5—5 of FIG. 4; and FIG. 6 is an end view of the dispensing end of the insertion device depicted in FIGS. 4 and 5 taken along line 6—6 of FIG. 5.

DESCRIPTION OF THE PREFERRED EMBODIMENT

Figure 7:
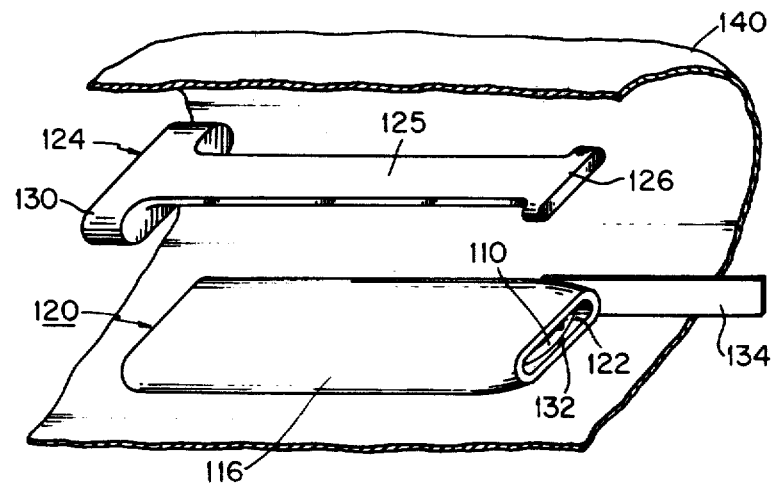
FIG. 7 is a perspective view of another embodiment of the inserting device.

Referring initially to FIGS. 2 and 3, the insertion device of this invention is adapted to insert into the vaginal canal a diaphragm, generally designated (10). The diaphragm (10) as indicated in FIG. 3 is generally dome-shaped and is formed of a thin impervious material which is smooth and resistant to tearing. Various materials may be employed for this purpose, preferred however is a thin latex material. The diaphragm (10) may be stiffened slightly along its rim (12) if desired, by means of a resilient member, for example a circular coil spring, a ring formed of a thin strip of sheet metal, or preferably a latex material similar to that of which the dome or center of the diaphragm is made. Preferably the diaphragm is constructed in a manner and by a process which permits it to be comparatively inexpensive and thus may be disposed of after only one use.

Referring to FIG. 1, the insertion device of this invention, generally designated (20), is of sufficient length for insertion of the instrument into the vagina in the position shown, i.e. the dispensing end of the device (20)

is disposed at the posterior cul-de-sac (A). As the diaphragm (10) is positioned by the movement of the elongated hollow member (16) toward the anterior cul-de-sac (B), a broader side (either top or bottom) of the diaphragm (10) is disposed toward the cervix (C). The insertion device (20) is long enough so that it extend beyond the vaginal canal when properly positioned.

Referring more particularly to FIGS. 4, 5 and 6, the insertion device (20) includes an elongated hollow member (16). Preferably, as indicated the hollow member (16) is slightly flattened, so as to have an oval cross section, to permit ease of insertion of the member (16) into the vaginal canal and to enable orientation of the member (16) and thereby enable the proper orientation of the diaphragm (10).

The hollow member (16) has a chamber (18) for holding the diaphragm (10) in compressed eleptical configuration. The compressed diaphragm is oriented with its longer axis parallel to the longitudinal axis of the hollow member and its shorter axis parallel to the plane of the greatest width of the hollow member. The flexible central portion of the diaphragm will deform as necessary to accomodate to the shape of the hollow member. This is more clearly depicted in FIGS. 4 and 5. Since the diaphragm (10) is compressed into the chamber (18), when released into the vaginal canal, the rim (12) of the diaphragm (10) springs outward to hold the diaphragm in position against the vaginal walls.

The chamber (18) for the diaphragm need not be any higher or thicker than the thickness of the diaphragm providing there is sufficient area to permit dispensing of the diaphragm (10). The chamber (18) additionally should be designed so that it is impervious to a spermacidal agent such as a jelly or cream which may be included in the chamber (18). In addition to the spermacidal properties, the cream or jelly also acts as a lubricant to facilitate dispensing of the diaphragm from the elongated tube.

An opening (22) is provided in one end of the elongated hollow member (16) through which the diaphragm (10) is dispensed. The opening as indicated in FIGS. 4 and 6 is also flattened, preferably oval in cross section, and substantially concentric to the oval cross section of the elongated hollow member (16). The opening (22) is positioned in such a manner so as to present the diaphragm (10) in the proper position near the cervix (C).

A plunger means (24) is slidably mounted within the hollow member (16) opposite the opening (22). The plunger means (24) is designed so that it slides through the chamber (18) dispensing the diaphragm (10) through the opening (22). As indicated in FIG. 5, the chamber (18) may be slightly larger than the plunger means (24). The pushing end 26 of the plunger means (24) is in contact with the diaphragm (10). The pushing end (26) is shaped to conform to the oval shape of the chamber (18). The pushing end (26) is larger than opening (19) in the back of chamber (18) and therefore prevents the plunger (24) from being removed from the hollow member (16) and seals the spermacidal agent in the chamber (18).

An indicia means, generally designated (28), is provided on the plunger means (24) for indicating the proper orientation of the diaphragm (10) for insertion. As indicated in FIG. 4, the plunger means (24) has a handle (30) at the end thereof which has written thereon, for example, "UP". This means that upon insertion of the device (20) in the vaginal canal, this indicia means (28) will be facing upward and capable of being viewed by the user. In order to perform this function, the plunger means (24), as mentioned above and as indicated in the depicted embodiment, should not rotate within the hollow member (16). Such an indicia means (28) permits the broad surface of the diaphragm (10) to be presented to the cervix (C).

The insertion device (20) is further provided with an indicia means for indicating the complete release of the diaphragm (10) from the opening (22). This may be done by several specific means: one means is to provide a plunger means (24) of a length such that it is sufficient to pass through the opening (22). Thus, referring to FIG. 4, when the handle (30) fully abuts the end of the hollow member (16), the end of the plunger means (24) extend to or slightly beyond opening (22). It is highly preferred, that in order to prevent any injury to the vaginal canal by the plunger means (24) that the end of the plunger means (24) not project too great a distance beyond the opening (22), but only a sufficient length to completely dispense the diaphragm (10).

Another indicia means for indicating complete release of the diaphragm (10) from the opening (22) is to provide at least one detent means in the opening (22) for inhibiting the complete dispensing of the diaphragm (10) from the opening (22). As indicated more clearly in FIG. 6, such a detent means can be two fingers (32) within the opening (22). Thus, when the rim (12) of the diaphragm (10) passes through the fingers (32), there is positive motion required to dispense the diaphragm (10), thus indicating complete release from the opening (22).

The two aforementioned indicia means for indicating complete release of the diaphragm (10) may be used in conjunction with each other.

As indicated in FIGS. 4 and 5, the insertion device (20) of this invention preferably has a removable closure means (34) for closing the opening (22). As indicated in FIGS. 4 and 5 this may be a simple removeable self-sticking tape. Such a closure means (34) maintains the diaphragm (10) and the spermacidal agent contained in chamber (18) in a sterile condition.

The insertion device (20) may be made of any suitable material, e.g. plastic, treated cardboard, etc. and is preferably disposable after only one use.

In use, one removes the closure means (34) from the opening (22) and inserts the hollow member (16) into the vaginal canal until the dispensing end of the hollow member (16) is disposed and pressed against the wall of the posterior cul-de-sac (A). The orientation indicia means (28), e.g. "UP", should be viewed by the user. The user then grasps the handle (30) with one hand, and the elongated hollow member (16) with the other hand, and moves the elongated member (16) towards the handle (30). When the plunger means (24) reaches the end of its stroke, i.e. when the handle (30) abuts the end of hollow member (16) and the end of the diaphragm has passed through the fingers (32), then the diaphragm is completely released and in the proper position covering the cervix (C).

Another Embodiment of The Invention

Figure 8:
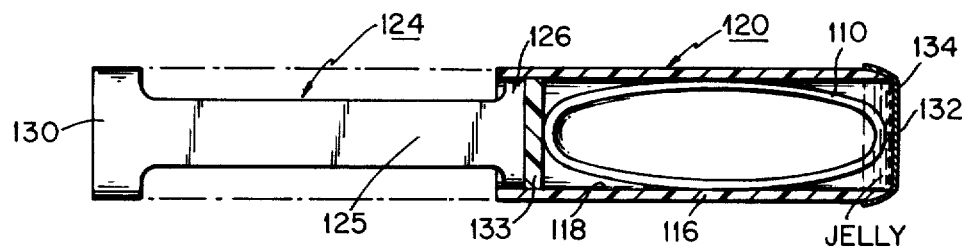
FIG. 8 is a longitudinal, cross sectional view of the insertion device depicted in FIG. 7 with the elements in operating relationship.
Figure 9:
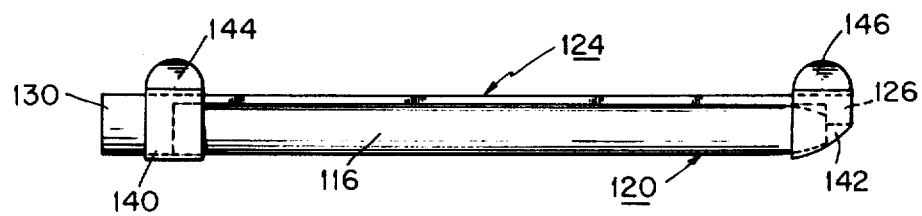
FIG. 9 is a side view of the embodiment shown in FIGS. 7 and 8, with the elements positioned for storage.

As shown in FIGS. 7, 8, and 9, another embodiment of the invention provides for an inserting device generally indicated at (120) having a hollow tubular member (116) in which a chamber (118) is formed for holding a diaphragm (110). The tubular member (116) may be oval in cross section. A plunger member (124) having a pushing end (126) and a handle (130) is positioned so that the stem (125) of the plunger lies on top of the hollow tube and the handle and pushing ends (130) and (126) respectively abut the ends of the hollow tube. The stem (125) of the plunger is offset with respect to the handle (130) and the pusher end (126) so that the inner surface of the handle (130) and the inner surface of the plunger extend downward from the stem leaving a clear uninterrupted surface for abutting the ends of the hollow tube. Note also that the pusher end (126) is slightly smaller than the handle (130) and also slightly smaller than the cross sectional shape of the hollow tube (116) so that the pusher end can be inserted into the rear of the hollow tube as shown in FIG. 8 in order to dispense the diaphragm (110). The container (116) may have a rear sealing member (133) and a removable closure means 134 in the front. The pusher end (126) of plunger (124) would then be placed against the rear seal (133) and the hollow tube (116) drawn rearward until the rear seal abutted the retaining fingers (132) on the front of the tube to fully dispell the diaphragm (110).

Prior to moving the hollow tube rearward, the removable closure means (134) at the front of the tube would be taken off to allow free exist of the diaphragm. Alternatively, the inner face of the handle (130) and the inner face of the pusher end (126) could be used to seal the back and front of the hollow tube (116) as shown in FIG. 9. The entire assembly could then be enclosed in a liquid proof, and if desired, airtight wrapping (140) such as cellophane, plastic or foil, in order to form a compact and easily carried item.

If no seals other than the plunger are employed, all that would be necessary in using the invention would be to remove the wrapper by means of any convenient tear strip or tear means that could be placed within the wrapper, lift off the plunger (124) while holding the tube in the other hand, insert the pusher end (126) in to the rear of the plunger, and then dispense the diaphragm. The jell or spermacidal agent in the tube would be viscous enough to remain the tube for the brief period of time between the removal of the wrapping and the placing of the hollow tube into the vaginal canal with the pusher end positioned in the back of the tube.

Another form of wrapping could be in the form of two adhesive strips (142) and (144) which band the ends of the device to seal the device to seal the handle (130) to the elongated member (116) at the rear, and similarly seal the pusher member to the dispensing end. Lift tabs (144) and (146) could be provided on each strip to facilitate its removal.

It will be understood that the various changes in the details, materials, arrangements of parts and operating conditions which have been described and illustrated in order to explain the nature of the invention, may be made by those skilled in the art within the principles and scope of the invention.

What is claimed is:

1. A diaphragm dispensing apparatus comprising:
   an elongated hollow member having a chamber for longitudinally holding a diaphragm and an opening on one end of said member through which said diaphragm is dispensed;
   a diaphragm resiliently compressed and held within said chamber of said elongated hollow member;
   a spermacidal agent in said chamber in contact with said diaphragm;
   a plunger means slidable within said hollow member at the other end of said member for dispensing said diaphragm through said opening;
   an indicia means on said plunger means for indicating the proper orientation of said diaphragm for insertion; and
   sealing means to seal said diaphragm within said chamber until dispensed by sliding of the plunger means within said hollow member.

2. A diaphragm dispensing apparatus comprising:
   an elongated hollow member having a chamber for longitudinally holding a diaphragm and one end of said member through which said diaphragm is dispensed;
   a diaphragm positioned within said chamber;
   a spermicidal agent in said chamber in contact with said diaphragm;
   a plunger means slidable within said hollow member dispensing said diaphragm through the dispensing end; and
   an indicia means on at least one of said plunger means and hollow member for indicating the proper orientation of said diaphragm for insertion.

3. The apparatus of claim 2, wherein said hollow member and said plunger are each substantially oval in cross-section and substantially concentric to each other.

4. The apparatus of claim 2, further comprising an indicia means for indicating complete release of said diaphragm from said dispensing end.

5. The apparatus of claim 2, wherein the length of said plunger means is sufficient to pass through the dispensing end of said elongated hollow member.

6. The apparatus of claim 5, wherein said dispensing end has at least one detent means for inhibiting the complete dispensing of the diaphragm from said dispensing end 7. The apparatus of claim 2, further comprising a removal closure means for closing said dispensing end.

8. The apparatus of claim 2, wherein:
   said elongated hollow member comprises an opening at the end remote from the end through which said diaphragm is dispensed;
   said plunger comprises:
   a handle;
   a pusher member; and
   a stem connecting the handle to the pusher member;
   said handle and pusher are connected to said stem to enable the handle and pusher member to simultaneously register with the dispensing end and the remote end of the elongated hollow member.

9. The apparatus of claim 8, wherein:
   the stem is approximately equal in length with the elongated hollow member and is disposed proximate the outer surface of the hollow member;
   the adjacent surfaces of the handle and pusher are constructed to act as closures for the dispensing end and remote end of the elongated hollow member.

10. The apparatus of claim 9, further comprising sealing means to seal the handle and pusher elements with the adjacent dispensing and remote ends of the elongated hollow member.

11. A diaphragm dispensing apparatus comprising:
    an elongated hollow member having a chamber for longitudinally holding a diaphragm and an opening on one end of said member through which said diaphragm is dispensed;
    a diaphragm positioned within said chamber;

a spermicidal agent in said chamber in contact with said diaphragm;

a plunger means slideable within said hollow member at the other end of said member for dispensing said diaphragm through said opening; and a removable closure means for closing said opening.

12. A diaphragm dispensing apparatus comprising:

an elongated hollow member having a chamber for longitudinally holding a diaphragm and an opening on one end of said member through which said diaphragm is dispensed;

a diaphragm positioned within said chamber;

a spermicidal agent in said chamber in contact with said diaphragm; and a plunger means slideable within said hollow member at the other end of said member for dispensing said diaphragm through said opening.

13. The apparatus of claim 11 or 12, wherein said hollow member and said plunger are each substantially oval in cross-section and substantially concentric to each other.

14. The apparatus of claim 11, or 12, further comprising an indicia means for indicating complete release of said diaphragm from said opening.

15. The apparatus of claim 11, or 12, wherein the length of said plunger means is sufficient to pass through said dispensing opening.

16. The apparatus of claim 15, wherein said dispensing opening has at least one detent means for inhibiting the complete dispensing of the diaphragm from said opening.

17. The apparatus of claim 11, or 12, wherein:

said elongated hollow member comprises an opening at the end remote from the end through which said diaphragm is dispensed;

said plunger comprises:

a handle;

a pusher member; and a stem connecting the handle to the pusher member;

said handle and pusher are connected to said stem to enable the handle and stem to simultaneously register with the openings at the ends of the elongated hollow member.

18. A diaphragm dispensing apparatus comprising:

an elongated hollow member having a chamber for longitudinally holding a diaphragm and an end of said member through which said diaphragm is dispensed and an end remote from the dispensing end;

a diaphragm positioned within said chamber;

a plunger means adapted to be slidably within said hollow member for dispensing said diaphragm through said dispensing end;

said plunger comprises:

a handle;

a pusher member; and a stem connecting the handle to the pusher member;

the stem approximately equals in length with the elongated hollow member and disposed proximate the outer surface of the hollow member;

said handle and pusher are connected to said stem to enable the handle and stem to simultaneously register with the dispensing and remote ends of the elongated hollow member; and the adjacent surfaces of the stem and pusher are constructed to act as closures for the dispensing and remote ends of the elongated hollow member.

19. A diaphragm dispensing apparatus comprising:

an elongated hollow member having a chamber for longitudinally holding a diaphragm and an end of said member through which said diaphragm is dispensed and an end remote from the dispensing end;

a diaphragm positioned within said chamber;

a spermicidal agent contained within said chamber;

a plunger means adapted to be slidable within said hollow member for dispensing said diaphragm through said dispensing end;

said plunger comprises:

a handle;

a pusher member; and a stem connecting the handle to the pusher member;

the stem approximately equals in length with the elongated hollow member and disposed proximate the outer surface of the hollow member;

said handle and pusher are connected to said stem to enable the handle and stem to simultaneously register with the dispensing and remote ends of the elongated hollow member; and the adjacent surfaces of the stem and pusher are constructed to act as closures for the dispensing and remote ends of the elongated hollow member.

20. A diaphragm dispensing apparatus comprising:

an elongated hollow member having a chamber for longitudinally holding a diaphragm and an end of said member through which said diaphragm is dispensed and an end remote from the dispensing end;

a spermicidial agent contained within said chambers;

a plunger means adapted to be slidable within said hollow member for dispensing said diaphragm through said dispensing end;

said plunger comprises:

a handle;

a pusher member; and a stem connecting the handle to the pusher member;

the stem approximately equals in length with the elongated hollow member and disposed proximate the outer surface of the hollow member;

said handle and pusher are connected to said stem to enable the handle and stem to simultaneously register with dispensing and remote ends of the elongated hollow member; and the adjacent surfaces of the stem and pusher are constructed to act as closures for the dispensing and remote ends of the elongated hollow member.

21. The apparatus of claim 18, 19, or 20, further comprising a sealing means disposed at each end of the apparatus to seal the handle and pusher element to the elongated hollow member.

22. The apparatus of claim 18, 19, or 20, wherein said hollow member and said plunger are each substantially oval in cross-section and substantially concentric to each other.

23. The apparatus of claim 18, 19, or 20, further comprising an indicia means for indicating complete release of said diaphragm from said opening.

24. The apparatus of claim 18, 19, or 20, wherein the length of said plunger means is sufficient to pass through said dispensing end.

25. The apparatus of claim 18, 19, or 20, wherein said dispensing end has at least one detent means for inhibiting the complete dispensing of the diaphragm from said dispensing end.

26. A diaphragm dispensing apparatus comprising:

an elongated hollow member having a chamber for longitudinally holding a diaphragm and one end of said member through which said diaphragm is dispensed and an opening at the other end which is remote therefrom;

a diaphragm positioned within said chamber;

a plunger means slideable within said hollow member dispensing said diaphragm through the dispensing end;

an indicia means on at least one of said plunger means and hollow member for indicating the proper orientation of said diaphragm for insertion;

said plunger comprises:

a handle;

a pusher member; and a stem connecting the handle to the pusher member;

said handle and pusher are connected to said stem to enable the handle and pusher member to simultaneously register with the dispensing end and the remote end of the elongated hollow member;

said stem approximately equal in length with the elongated hollow member and disposed proximate the outer surface of the hollow member;

said adjacent surfaces of the handle and pusher are constructed to act as closures for the dispensing end and remote end of the elongated hollow member.

27. The apparatus of claim 26, further comprising sealing means to seal the handle and pusher elements with the adjacent dispensing and remote ends of the elongated hollow member.

* * * * *